United States Patent [19]

Goettsche et al.

[11] Patent Number: 4,761,179
[45] Date of Patent: Aug. 2, 1988

[54] WOOD PRESERVATIVES

[75] Inventors: Reimer Goettsche, Baden-Baden; Hans-Norbert Marx, Buehl-Weitenung, both of Fed. Rep. of Germany

[73] Assignee: Dr. Wolman GmbH, Sinzheim, Fed. Rep. of Germany

[21] Appl. No.: 12,379

[22] Filed: Feb. 9, 1987

[30] Foreign Application Priority Data

Feb. 18, 1986 [DE] Fed. Rep. of Germany ....... 3605008

[51] Int. Cl.$^4$ ................................................. C09D 5/14
[52] U.S. Cl. ............................... 106/18.32; 106/15.05; 106/18.3; 424/166
[58] Field of Search ............ 424/166; 106/18.3, 18.32, 106/15.05; 514/494, 493, 573; 427/356

[56] References Cited

U.S. PATENT DOCUMENTS

| | | | |
|---|---|---|---|
| 3,435,039 | 3/1969 | Wakeman et al. | 106/18.32 |
| 3,810,767 | 5/1974 | Raff et al. | 106/18.31 |
| 4,143,153 | 3/1979 | Pommer et al. | 424/166 |
| 4,461,721 | 7/1984 | Goettsche et al. | 106/18.3 |
| 4,496,613 | 1/1985 | Zagefka et al. | 106/18.32 |
| 4,547,366 | 10/1985 | Marx | 514/461 |
| 4,622,248 | 11/1986 | Leach et al. | 424/166 |

FOREIGN PATENT DOCUMENTS 0089958 12/1985 European Pat. Off. .
2410603 12/1982 Fed. Rep. of Germany .

Primary Examiner—Paul Lieberman
Assistant Examiner—Helene Kirschner
Attorney, Agent, or Firm—Oblon, Fisher, Spivak, McClelland & Maier

[57] ABSTRACT

A wood preservative based on a water-dilutable formulation of the compound di-(N-cyclohexyldiazoniumdioxy)-copper, a polyamine, a complex-forming carboxylic acid and, if required, a salt having a fungicidal anion has a pH in the aqueous solution of not less than 7.5 in the conventional concentration for use.

6 Claims, No Drawings

WOOD PRESERVATIVES

The present invention relates to the provision of agents for the treatment of (solid) wood which are based on aqueous formulations of di-(N-cyclohexyldiazoniumdioxy)-copper, a polyamine and a complex-forming carboxylic acid and, if required, further components, in particular fungicidal salts whose action is due to the anion, eg. borates.

It is known that wood can be impregnated with water-soluble complexes of di-(N-cyclohexyldiazoniumdioxy)-copper (abbreviated to Cu-HDO); previous name: N-nitrosocyclohexylhydroxylamine copper salt).

Among the known complex formers, the polyamines, eg. ethylenediamine, diethylenetriamine and dipropylenetriamine, are particularly suitable for the preparation of water-soluble complexes. In the impregnation of wood by the large-scale industrial method, the pressure process, with aqueous solutions of the known-soluble complexes, it was found that the penetration and the distribution of the Cu-HDO preservative was not sufficient to ensure in the long term the necessary wood preservation, for example in the case of round timber, such as masts or palisades, where these are used in contact with earth (eg. as telegraph poles). In thoroughly impregnated pine round timber with adequate sapwood (more than 3 cm), the Cu-HDO penetration achieved was only 10–15 mm. The alkaline solutions of the complexed Cu-HDO (pH about 9–10) evidently reacted with the acidic wood components at as early a stage as impregnation, so that the solutions could not penetrate deep into the wood.

On the other hand, the complex-forming capacity of acidic complex formers of copper, such as tartaric acid, lactic acid, nitrilotriacetic acid and other amines, eg. monoamines such as ethanolamine, is not sufficient to give stable aqueous, acidic or alkaline solutions of Cu-HDO. The Cu-HDO is precipitated from the aqueous solutions after the latter have stood for shorter or longer times.

We have found that the abovementioned disadvantages are not encountered if impregnation is carried out using an aqueous solution obtained from a wood preservative by dilution with water, the said wood preservative containing, in addition to Cu-HDO, a polyamine and a complex-forming carboxylic acid in an amount such that, when the preservative is diluted with water to a conventional treatment concentration of from 0.3 to 1.5% by weight of copper, the pH of the aqueous solution is not less than 7.5.

A polyamine is, for example, a diamine or triamine, eg. diethylenetriamine(2,2'-diaminodiethylamine) or dipropylenetriamine(3,3'-diaminodipropylamine). Ethylenediamine, 1,2-propylenediamine and 1,3-diaminopropane can also be used, but the wood preservatives (concentrates) prepared with these crystallize out at fairly low temperatures (0° C.) with the formation of solid crystals and are therefore unsuitable for use (for dilution with water) under these conditions.

A complex-forming carboxylic acid is a carboxylic acid which forms complexes with copper compounds, for example a hydroxycarboxylic acid, eg. lactic acid or tartaric acid, or a nitrogen-containing complex-forming polycarboxylic acid, eg. nitrilotriacetic acid.

The wood preservatives can also contain an alkanolamine, eg. ethanolamine, aminoethylethanolamine or isopropanolamine, a compound having a fungicidal anion, for example a boron compound, such as a borate, eg. borax, boric acid or ammonium tetrafluoroborate, or a quaternary ammonium salt, or a mixture of these substances.

The water-dilutable agents contain the copper, calculated as the element, in concentrated form, in general in an amount of from 1 to 15 percent by weight.

Suitable concentrates contain, for example,
from 5 to 50% by weight of Cu-HDO,
from 5 to 40% by weight of a polyamine,
from 5 to 30% by weight of a complex-forming carboxylic acid,
not more than 20% by weight of a compound having a fungicidal anion,
not more than 20% by weight of an alkanolamine and
not more than 50% by weight of a quaternary ammonium salt, the sum of the percentages being 100, and, if required, minor amounts of other components, such as amines, ammonia, corrosion inhibitors and, if necessary, water, the amount of which however can generally be kept low and essentially facilitates handling. However, the invention also extends to the impregnating solutions of appropriately lower specific concentration, which can be prepared by dilution with water.

As a result of complex formation with the polyamine and the penetration of the wood preservative, the penetrating power of the said preservative is increased, the impregnatable parts of the wood are completely impregnated and the wood is adequately protected.

Adding boric acid to the novel preservatives also protects, by diffusion, regions of the wood which are not accessible to impregnation (heartwood).

The preservatives according to the invention can also be readily mixed with quaternary ammonium compounds.

Examples of suitable quaternary ammonium salts are those of the general formula $(R^1R^2R^3R^4N)^+Z^-$ where
$R^1$ is alkyl of 8 to 20 carbon atoms, alkenyl of 12 to 20 carbon atoms or benzyl which is unsubstituted or substituted by $C_1$–$C_{20}$-alkyl or halogen,
$R^2$ and $R^3$ are each $C_1$–$C_6$-alkyl,
$R^4$ is $C_1$–$C_{20}$-alkyl, or two of the radicals $R^1$ to $R^4$ together with the nitrogen atom form a heterocyclic radical which contains 4 or 5 carbon atoms, 1 or 2 nitrogen atoms and one or two double bonds, the carbon atoms being unsubstituted or substituted by $C_1$–$C_4$-alkyl or halogen, and Z is an acid radical.

Dissolving the copper compound in the polyamine and the complex-forming carboxylic acid, if necessary with the addition of water, gives highly concentrated water-soluble pastes or liquid concentrates which, when dissolved in water, can be used for impregnating wood. The pH of aqueous impregnating solutions is in general from 8.0 to 10.0, in particular from 8.5 to 9.5. By adding acids, the solution can, if required, also be brought to a pH of about 8 or less. A precondition is that the precipitation of the Cu-HDO begins at a pH which is lower by not less than 1 (concentration-dependent).

The amount of polyamines and complex-forming carboxylic acids used is such that, on the one hand, it is sufficient for complex formation of the copper and, on the other hand, salts of the additionally used fungicidal anions (borate, fluoroborate) may form, so that the pH of the aqueous impregnating solution is 7.5 or more, preferably from 8.5 to 9.5.

The Examples which follow illustrate the invention.

I. DESCRIPTION OF THE EXPERIMENTAL PROCEDURE

Spruce round timber which had been mechanically pretreated by the boring method was used for the experiments. The round timber was impregnated by the pressure process and had a length of 1.20 m and a mean diameter of 0.20 m, the length of the perforated section being 0.90 m and the perforation depth 3 cm). Because of its cell structure, spruce wood is difficult to impregnate. However, mechanical perforation improves its impregnation properties. In the case of round timber (eg. masts), uniform penetration is achieved for a perforation of 3 cm, for example when chromium-copper-boron salts are used. The perforated section of the timber is installed in the particularly endangered region of the earth/air zone. The perforated zone is sensitive to reduced penetrating capacity of a wood preservative and is therefore a measure of the penetrating power of an aqueous wood preservative.

For long-lasting wood preservation in the case of masts and other round timber in contact with the earth, the limiting value of the fungicidal action against Basidiomycetes fungi must be reached in the second centimeter (measured from the surface) in the earth/air region after washout.

To test the efficiency of wood preservation, the impregnated round timber was left to lie for four weeks to achieve adequate fixing. 5 cm wide mast disks were then cut from the perforated region. From these mast disks, wooden blocks measuring 1.5×2.5×5 cm were then removed to check for fungi. The blocks were taken at distances of 0, 0.5 and 1.0 cm from the surface, thus covering the impregnated region from 0 to 1.5 cm, from 0.5 to 2.0 cm and from 1.0 to 2.5 cm. The blocks removed are used to measure the penetrating power of the wood preservative and consequently the efficiency. By biological testing of the efficiency, it can be determined from these blocks whether the depth of penetration of the wood preservative is sufficient to meet the above requirement, ie. protection from Basidiomycetes fungi in the second centimeter after washout. The blocks were therefore thoroughly washed and then checked for the wood-destroying Basidiomycetes *Coniophora puteana* and *Poria monticola*. The degree of destruction was assessed.

II. TEST EXAMPLES

| | |
|---|---|
| 0 | no destruction |
| + | slight attack |
| ++ | moderate attack |
| +++ | severe attack |
| ++++ | complete destruction |

EXAMPLE I

Comparative example (not according to the invention)
25% of Cu-HDO
15% of diethylenetriamine(2,2'-diaminodiethylamine)
60% of water 20 g of this mixture are diluted with water to give 1 liter of solution (designated as use concentration of 2% below).
Test for fungi after washing:

| Perforated region | Degree of destruction | |
|---|---|---|
| Depth | *Coniophora puteana* | *Poria monticola* |
| 0–1.5 cm | + | 0 |
| 0.5–2.0 cm | ++ | + |
| 1.0–2.5 cm | ++++ | +++ |

EXAMPLE 2

(according to the invention)

25.0% Cu-HDO
22.5% diethylenetriamine
12.5% nitrilotriacetic acid
40.0% of water
Use concentration 2.0%.
Test for fungi after washing:

| Perforated region | Degree of destruction | |
|---|---|---|
| Depth | *Coniophora puteana* | *Poria monticola* |
| 0–1.5 cm | 0 | 0 |
| 0.5–2.0 cm | 0 | 0 |
| 1.0–2.5 cm | 0 | 0 |

EXAMPLE 3

25.0% Cu-HDO
30.0% dipropylenetriamine
12.5% nitrilotriacetic acid
12.5% boric acid
20.0% of water
Use concentration 2.0%.
Test for fungi after washing:

| Perforated region | Degree of destruction | |
|---|---|---|
| Depth | *Coniophora puteana* | *Poria monticola* |
| 0–1.5 cm | 0 | 0 |
| 0.5–2.0 cm | 0 | 0 |
| 1.0–2.5 cm | + | 0 |

EXAMPLE 4

25.0% Cu-HDO
12.5% diethylenetriamine
12.5% ethanolamine
12.5% boric acid
12.5% nitrilotriacetic acid
25.0% of water
Use concentration 2.0%.
Test for fungi after washing:

| Perforated region | Degree of destruction | |
|---|---|---|
| Depth | *Coniophora puteana* | *Poria monticola* |
| 0–1.5 cm | 0 | 0 |
| 0.5–2.0 cm | 0 | 0 |
| 1.0–2.5 cm | 0 | + |

EXAMPLE 5

25.0% Cu-HCO
17.5% diethylenetriamine
5.0% of ethanolamine
12.5% tartaric acid
12.5% boric acid
27.5% of water Use concentration 2.0%.
Test for fungi after washing:

| Perforated region Depth | Degree of destruction | |
| --- | --- | --- |
| | *Coniophora puteana* | *Poria monticola* |
| 0–1.5 cm | 0 | 0 |
| 0.5–2.0 cm | 0 | 0 |
| 1.0–2.5 cm | + | + |

EXAMPLE 6

25.0% Cu-HDO
12.5% dipropylenetriamine
15.0% of aminoethylethanolamine
12.5% nitrilotriacetic acid
12.5% boric acid
22.5% of water Use concentration 2.0%.
Test for fungi after washing:

| Perforated region Depth | Degree of destruction | |
| --- | --- | --- |
| | *Coniophora puteana* | *Poria monticola* |
| 0–1.5 cm | 0 | 0 |
| 0.5–2.0 cm | 0 | 0 |
| 1.0–2.5 cm | 0 | 0 |

The novel wood preservatives containing Cu-HDO are liquid, more or less viscous concentrates which are stable even at 0° C. and do not crystallize out.

It is also possible to use isopropanolamine mixed with the polyamines, but for economic reasons it is advisable to use ethanolamine.

The mixtures according to the invention can be colored by water-soluble dyes for monitoring purposes; water-insoluble dyes can be used in solution in solvents or together with emulsifiers as dye emulsions.

The novel wood preservatives can, if required, contain additional conventional components, such as corrosion inhibitors, eg. isononanoic acid or its salts.

We claim:

1. A wood preservative based on a water-dilutable formulation of the compound di-(N-cyclohexyldiazonium-dioxy)-copper, wherein the wood preservative contains a polyamine and a tartaric acid or nitrogen-containing polycarboxylic acid in an amount such that, when the preservative is diluted with water to a conventional treatment concentration of from 0.3 to 1.5% by weight of copper, the pH of the aqueous solution is not less than 7.5.

2. A wood preservative as claimed in claim 1, which additionally contains an alkanolamine.

3. A wood preservative as claimed in claim 1, which additionally contains ethanolamine.

4. A wood preservative as claimed in claim 1, which additionally contains a borate or boric acid.

5. A wood preservative as claimed in claim 1, which additionally contains a quaternary ammonium salt.

6. A process for pressure impregnation of wood by treating wood with an aqueous solution of a wood preservative as claimed in claim 1 which has a pH of not less than 7.5.

* * * * *